(12) United States Patent
Berners-Price et al.

(10) Patent No.: US 6,218,378 B1
(45) Date of Patent: *Apr. 17, 2001

(54) ANTI-TUMOR AGENTS COMPRISING PYRIDYL-SUBSTITUTED METAL-DIPHOSPHINE COMPLEX

(75) Inventors: Susan Jane Berners-Price, Paddington; Richard John Bowen, Cleveland; Peter Gordon Parsons, St. Lucia, all of (AU)

(73) Assignee: Griffith University, Queensland (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/860,518
(22) PCT Filed: Dec. 11, 1995
(86) PCT No.: PCT/AU95/00833
  § 371 Date: Aug. 22, 1997
  § 102(e) Date: Aug. 22, 1997
(87) PCT Pub. No.: WO96/17855
  PCT Pub. Date: Jun. 13, 1996

(30) Foreign Application Priority Data

Dec. 9, 1994 (AU) ........................... PM 9976
Jul. 17, 1995 (AU) ........................... PN 4176

(51) Int. Cl.[7] .................. A01N 55/02; A61K 31/555; C07F 1/10; C07F 1/12
(52) U.S. Cl. .................. 514/188; 514/188; 546/2
(58) Field of Search .................. 546/2; 514/188

(56) References Cited

U.S. PATENT DOCUMENTS

| | | | |
|---|---|---|---|
| 4,716,230 | * 12/1987 | Hill | 546/21 |
| 4,902,675 | * 2/1990 | Hill et al. | 514/24 |
| 5,037,812 | * 8/1991 | Berners-Price et al. | 514/105 |

FOREIGN PATENT DOCUMENTS

| | | |
|---|---|---|
| 2262284A | 6/1993 | (GB) . |
| 96/17856 | * 6/1998 | (WO) . |

OTHER PUBLICATIONS

Berners–Price et al. Gold Phosphine complexes as antitumour agents. J. Med. Chem. 33(5), 1386–1392, (1990).*
Bowen et al., "Convenient synthetic routes to bidentate and monodentate 2–, 3– and 4–pyridyl phosphines: potentially useful ligands for water–soluble complex catalysts," J. Organometallic Chemistry, vol. 554, pp. 181–184, 1998.*
Leo et al., "Partition Coefficients and Their Uses," Chemical Reviews, vol. 71, No. 6, pp. 525–616, Dec. 1971.*
Berners–Price et al., "Cytotoxicity and Antitumor Activity of Some Tetrahedral Bis(diphosphino)gold(I) Chelates," J. Med. Chem., vol. 33, No. 5, pp. 1386–1392, May 1990.*
Berners–Price, et al.; Journal of the Chemical Society; 1999, 1–10;Dalton Transactions.
Berners–Price, et al.; J.Chem.Soc, 1998; pp 1743–1750; Silver(i) Nitrate Adducts with Bidentate 2–, 3– and 4–Pyridyl Phosphines. Solution $^{31}$P and [$^{31}$P–$^{109}$Ag] NMR Studies of 1:2 Complexes and Crystal Structure of Dimeric [{Ag(d2pype)(υ–d2pype)}$_2$]–[NO$_3$]$_2$;$_{2CH2Cl2}$ [d2pype=1, 2–bis(di–2pyridylphosphino)Ethane].
Berners–Price, et al.; Dept. of Chemistry, Birkbeck College, University of London; pp 29–102; Phosphines and Metal Phosphine Complexes:Relationship of Chemistry to Anticancer and Other Biological Activity (1988).

* cited by examiner

Primary Examiner—Mukund J. Shah
Assistant Examiner—Ben Schroeder
(74) Attorney, Agent, or Firm—Knobbe, Martens, Olson & Bear, LLP (57) ABSTRACT

A method of treatment or inhibition of tumors including the steps of: (i) exchanging one or more of the eight phenyl substituents in the compound [M(dppe)$_2$]$^+$ where M is selected from Au(I), Ag(I) and Cu(I) by 2, 3, or 4 pyridyl substituents to provide a compound having anti-tumor activity and an octanol/water partition coefficient between 0.01 and 25.5; and (ii) administering said compound to a subject requiring treatment which compound has selective toxicity to cancer cells including cisplatin resistant human carcinoma cell lines. The invention also includes within its scope compounds of formula (I)

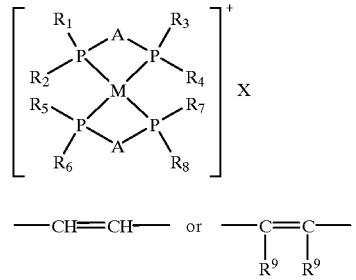

(I)

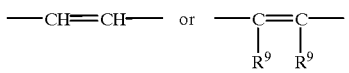

(a)

wherein $R_1$, $R_2$, $R_3$, $R_4$, $R_5$, $R_6$, $R_7$ and $R_8$ are the same or different and may be selected from phenyl, 4-pyridyl, 3-pyridyl, 2-pyridyl wherein each of the 4-pyridyl, 3-pyridyl and 2-pyridyl may optionally be substituted; A is selected from —(CH$_2$)— wherein n is 2 or 3 or cis —CH=CH— or (a) where R$^9$ represents carboxylate and in such case $R_1$, $R_2$, $R_3$, $R_4$, $R_5$, $R_6$, $R_7$ and $R_8$, may be all phenyl; M is Au(I), Ag(I) or Cu(I); X is monovalent anion such as nitrate or bromide, chloride, iodine or any other non-toxic anion; with the following provisos: (i) $R_1$ through $R_8$ cannot be all phenyl; (ii) when $R_1$ through $R_8$ is 2-pyridyl, and A is —(CH$_2$)$_2$—, M cannot be Au(I); or (iii) when $R_1$ through $R_8$ is the same and is 4-pyridyl, X is Cl and A is —(CH$_2$)$_2$—, M cannot be Au(I).

9 Claims, 8 Drawing Sheets

ANTI-TUMOR AGENTS COMPRISING PYRIDYL-SUBSTITUTED METAL-DIPHOSPHINE COMPLEX

FIELD OF THE INVENTION

THIS INVENTION relates to metal complexes of aryl phosphines and processes for their preparation.

BACKGROUND OF THE INVENTION

Although platinum anti-cancer drugs are currently the only metal compounds in clinical use for cancer chemotherapy, many other metal complexes have shown high antitumour activity in animal models. There is great scope for the design of metal antitumour drugs that may be less toxic and more effective than platinum complexes.

Previous work contributed to the identification of certain metal diphosphine complexes as a potential new class of anti-cancer agents. In particular, the Au(I) complex [Au(dppe)$_2$]Cl (where dppe is 1,2-bis(diphenylphosphino) ethane) showed good antitumour activity against a range of tumour models in mice as disclosed in Berners-Price et al., 1986, Cancer Research 46 5486–5493. Structure activity relationships have been evaluated for a wide range of diphosphine ligands and their metal complexes as disclosed in Berners-Price et al., 1988, Structure Bonding (Berlin) 70 27–102. For complexes of the type [Au(R$_2$P(CH$_2$)$_n$PR'$_2$)$_2$]X highest activity was found where R=R'=phenyl and n=2,3 or the cis-CH=CH analogue. In general, activity was reduced, or lost altogether when the phenyl substituents on the phosphine were replaced by other substituents, but retained when Au(I) is substituted by Ag(I) or Cu(I). Dppe complexes of other metals (e.g. Pt(II) and Pd(II)) were found to be less active than the phosphine alone as shown in Khohkar et al., 1990, Inorg. Biochem. 39 117 and Mirabelli et al., 1987, J. Med. Chem. 30 2181. Since the tetrahedral complexes of the Group 11 metal ions have kinetically labile M—P bonds it is possible that the metal acts as a delivery system for the cytotoxic diphosphines. The mechanism of the cytotoxic activity is, however, still unknown, although the available evidence indicates that the primary cytotoxic lesion may arise from damage to nuclear chromatin. [Au(dppe)$_2$]$^+$ produced DNA-single strand breaks and DNA-protein crosslinks in tumour cells, with the latter being the critical lesions at low concentrations (Berners-Price et al., (1986) above).

Clinical development of [Au(dppe)$_2$]Cl was precluded following the identification of severe cardiac, hepatic and vascular toxicities in preclinical trials in Beagle dogs as described in Rush et al., 1987, Toxicologist 7 59 and Hoke et al., 1989, Toxicol. Appl. Pharmacol. 100 293. These toxicities have been attributed to disruption of mitochondrial function as described in Hoke et al., 1988, Biol. Chem. 262 11203. [Au(dppe)$_2$]$^+$ is a cation with eight hydrophobic phenyl substituents and these properties promote dissolution of the complex in the mitochondrial membrane where it uncouples oxidative phosphorylation via dissipation of the membrane potential.

Reference also may be made to Berners-Price et al., 1990, J. Med. Chem. 33 1386 which refers to cytotoxicity and anti-tumour activity of bis(diphosphino) gold chelates and, in particular, with 2- and 4-pyridyl substituents. The 2-pyridyl substituted chelates were found to demonstrate anti-tumour activity in mice while the 4-pyridyl substituted chelates were inactive.

Metal complexes of aryl phosphines are disclosed in EP0164970 and in EP0198696. EP0164970 discloses a process for preparing a pharmaceutical composition which comprises combining an inert pharmaceutically acceptable carrier or diluent with an effective tumour cell growth inhibiting amount of a metal complex of a bidentate phenyl phosphine. However, such compounds have since been shown to develop severe cardiac hepatic and vascular toxicities in pre-clinical trials in Beagle dogs as described above.

EP0198696 discloses gold complexes of a bidentate pyridyl phosphine and compositions containing same and their use as tumour cell inhibitors. However, as will be demonstrated hereinafter, the structure of such complexes of bidentate pyridyl phosphines are not believed to be correct and hence this creates difficulties in clinical assessment of such compounds.

Further progress in the development of metal phosphine antitumour drugs depends on being able to separate the anti-tumour effects from toxic side effects. A major difficulty would appear to be that the presence of phenyl substituents promotes the mitochondrial toxicity, but structure activity relationships suggest that these phenyl groups are important for cytotoxic activity.

The introduction of cisplatin and other platinum-based drugs into the clinical treatment of cancer has resulted in dramatic improvements in the response rates for some tumour types, in particular, testicular, ovarian and bladder cancers. A major clinical limitation to their efficacy is the occurrence of tumours that are resistant to these drugs. The potential significance of this research is that metal phosphine anti-tumour drugs appear to have a different mechanism of action to other drugs in clinical use. Providing the unfavourable toxic side effects can be overcome these compounds offer great potential value for combination chemotherapy or for treatment of cancers that are resistant to other anti-cancer drugs and, in particular, cisplatin.

SUMMARY OF THE INVENTION

It is therefore an object of the invention to provide a method of treatment or inhibition of tumours using metal complexes of aryl phosphines which have selective toxicity in relation to cancer cells including cisplatin resistant human carcinoma cells lines.

A further object of the invention is to provide new metal complexes of aryl phosphines having the same clinical effect as described above.

The invention therefore in one aspect provides a method of treatment or inhibition of tumours including the steps of:

(i) exchanging one or more of the eight phenyl substituents in the compound [M(dppe)$_2$]$^+$ where M is selected from Au(I), Ag(I) and Cu(I) by 2, 3, or 4 pyridyl substituents to provide a compound having anti-tumour activity and an octanol/water partition co-efficient between 0.01 and 25.5; and

(ii) administering said compound to a subject requiring such treatment which compound has selective toxicity to cancer cells including cisplatin resistant human carcinoma cell lines.

Compounds which have particular relevance to the present invention are covered by the following formula:

(I)

wherein $R_1$, $R_2$, $R_3$, $R_4$, $R_5$, $R_6$, $R_7$ and $R_8$ are the same or different and may be selected from phenyl, substituted phenyl, 4 pyridyl, 3-pyridyl, 2-pyridyl wherein each of the 4-pyridyl, 3-pyridyl and 2-pyridyl may optionally be substituted;

A is selected from —(CH$_2$)—$_n$ where n is 2 or 3 or cis —CH=CH— or where $R^9$ represent carboxylate and in such case $R_1$, $R_2$, $R_3$, $R_4$, $R_5$, $R_6$, $R_7$ and $R_8$ may be all phenyl;

M is Au(I), Ag(I) or Cu(I);

X is monovalent anion such as nitrate or halide or any other non-toxic anion;

with the following provisos:
(i) $R_1$ through $R_8$ cannot be all phenyl; or
(ii) that when $R_1$ through $R_8$ is 2-pyridyl, and A is —(CH$_2$)$_2$— M cannot be Au(I).

The invention also includes within its scope new compounds of formula (I) above with the proviso that when $R_1$ through $R_8$ is the same and is 4-pyridyl, X is Cl and A is —(CH$_2$)$_2$— M cannot be Au(I).

It is stressed that likely substituents on the phenyl or pyridyl ring are unlikely to adversely affect the anti-tumour activity of the compounds provided that (i) the metal complexes of these substituted phosphines are stable, (ii) the complexes retain the cationic properties, and (iii) the complexes are within the range of partition co-efficients 0.01–25.5.

With regard to anions, EP0164970 indicates that for complexes of formula I, the nature of the anion does not greatly influence the anti-tumour activity. Under physiological conditions, the anion will be readily displaced by chloride which is present at concentrations up to 154 mM.

By the term "non-toxic anion" is meant any anion which has minimal or benign toxicity as discussed in U.S. Pat. No. 5,037,812. Preferred anions are those available in pharmaceutical or food grade. The pharmaceutical acceptability of a particular anion can be determined by conventional techniques for determining toxicology. Suitable pharmaceutically acceptable anions include monocarboxylates (e.g. formate, acetate, lactate, hippurate, amino acids), di and tri-carboxylates (e.g. malonate, citrate), phosphate and phosphate esters, phospholipids, sulphate, carbonate, bicarbonate, halide, nitrate, PF$_6$, methanesulfonate, 2-hydroxypropanoate, glucuronate, cyanate, citrate, trifluoromethane-sulfonate, 2-oxopropanoate, 4-hydroxylbutanoate, hydroxy-acetate, 2-hydroxybutanoate, 2,3-dihydroxypropanoate, 2-hydroxyethyl sulfonate (isethionate), 2-hydroxypropanoate (lactate), 2-oxopropanoate, hydroxyacetate and 2,3-dihydroxypropanoate.

Appropriate substituents on the phenyl ring include nitro, sulphonate, halogen, $C_{1-4}$ alkyl, haloalkyl, alkoxy inclusive of methoxy and ethoxy, acyl (e.g. acetyl), amino, acylamino, alkylamino, aldehyde, hydroxy, hydroxyalkyl and derivatives thereof, thiol, thiol substituted with $C_{1-4}$ alkyl, amide, keto, carboxylate, sulphoxy, sulphoxyalkyl, sulphoxide, sulphone, amide derivatives with $C_{1-4}$ alkyl substituent, sulphate esters, hydroxyesters, phosphate esters, carboxylic acid esters inclusive of acetate, sulphonic acid and phosphinic acid. Suitable substituents may include sulphonate, halogen, nitro, $C_{1-4}$ alkyl, amino, aldehyde, alkyamino, haloalkyl, hydroxy, alkoxy inclusive of methoxy and ethoxy, hydroxyalky, sulphoxy, thiol, thiol substituted with $C_{1-4}$ alkyl, aminde, keto carboxylate including di- and tri-carboxylate suitable substituents on the pyridyl ring may include oxygen, hydrogen, nitro, sulphonate, halogen, acyl or alkyl on the nitrogen-atom. Suitable substituents on one or more C atom of the pyridyl ring include nitro, sulphonate, halogen, $C_{1-4}$ alkyl, haloalkyl, alkoxy inclusive of methoxy and ethoxy, acyl (e.g. acetyl), amino, acylamino, alkylamino, aldehyde, hydroxy, hydroxyalkyl and derivatives thereof, thiol, thiol substituted with $C_{1-4}$ alkyl, amide, keto, carboxylate, sulphoxy, sulphoxyalkyl, sulphoxide, sulphone, amide derivatives with $C_{1-4}$ alkyl substituent, sulphate esters, hydroxyesters, phosphate esters, carboxylic acid esters inclusive of acetate, sulphonic acid and phosphinic acid.

Preferred compounds of formula I include the following:
(i) wherein at least one of $R_1$ through $R_8$ is 3-pyridyl;
(ii) wherein all of $R_1$ through $R_8$ is 3-pyridyl;
(iii) wherein $R_1$, $R_2$, $R_5$ and $R_6$ is phenyl or substituted phenyl and $R_3$, $R_5$, $R_7$ and $R_8$ is 2-pyridyl;
(iv) wherein M is Ag(I) or Cu(I).

In regard to compounds of formula I, the 4-pyridyl complex where $R_1$ through $R_8$ is 4-pyridyl was disclosed in reference EP0198696 as—having insignificant anti-tumour activity. This reference also discloses the 2-pyridyl complexes where $R_1$ through $R_8$ is the same and is 2-pyridyl, where M=Au(I), X is halo and A is a straight or branched chain alkanediyl chain of from 1–6 carbon atoms) for use in therapy for inhibiting the growth of animal tumour cells.

The synthesis of the 4-pyridyl complex (where M=Au(I), A=(CH$_2$)$_2$ and X≈Cl⁻) is described in Berners Price et al. (1990) above but was found to be inactive in mice bearing (i) i.p. P388 leukaemia, and (ii) M5076 Reticulum Cell Sarcoma.

The abovementioned compounds of formula (I) above may be prepared from ligands of the structure (II)

where $R_1$, $R_2$, $R_3$ and $R_4$ are the same or different and are selected from phenyl, substituted phenyl wherein the substituents are preferably as defined above in regard to $R_1$ through $R_8$, 2-pyridyl, 3-pyridyl or 4-pyridyl wherein each of 2-pyridyl, 3-pyridyl and 4-pyridyl may optionally be substituted; and A is —(CH$_2$)$_n$— where n is 2 or 3, cis(—CH=CH) or wherein $R^9$ is carboxylate with the provisos:

(i) that when A is —(CH$_2$)$_2$—, and R$_1$, R$_2$, R$_3$ and R$_4$ are the same, they cannot be 4-pyridyl or 2-pyridyl; and (ii) when R$_1$ and R$_3$ are phenyl, A is —(CH$_2$)$_2$—, R$_2$ and R$_4$ cannot both be 2-pyridyl.

In regard to synthesis of compounds of formula (I) where M is Au(I) and X is chloride, such compounds are conveniently prepared by reacting the appropriate ligand of formula (II) with sodium tetachloroaurate reduced in in situ to gold (I) by thiodiglycol or other suitable methods which include reacting the appropriate ligand of formula (II) with a suitable gold (I) compound such as Au(CO)Cl or Bu$_4$NAuCl$_2$. In the case where M is Ag(I) or Cu(I), use may be made of a suitable Ag(I) or Cu(I) reactant, for example, silver nitrate or cuprous chloride. In the case where X is other than halide or nitrate, use can be made of suitable starting compound which includes the relevant anion or by metathesis of halide or nitrate anion in an appropriate non-reactive solvent.

To prepare all compounds of formula (I) where X is other than chloride, reference should be made to EP0164970 and 0198696.

The invention encompasses Au(I), Ag(I$^-$) and Cu(I) complexes of bidentate pyridyl phosphines of formula (II) above which includes not only compounds of formula (I) alone but also compounds of the following formulae (III), (IV) and (V) hereunder:

(III)

where R is 2-pyridyl or substituted 2-pyridyl, M is Au(I), Ag(I) or Cu(I);

X may be monovalent or divalent; and

A is selected from —(CH$_2$)$_2$—, —(CH$_2$)$_3$— or —CH=CH—;

(IV)

where R is 2-pyridyl or substituted 2-pyridyl, M is Au(I), Ag(I) and Cu(I); and

X is monovalent, divalent or trivalent or a mixture thereof and A is —(CH$_2$)$_2$—, —(CH$_2$)$_3$— or cis-CH=CH—; or (V)

where R$_1$ through R$_8$ may be the same or different and may be 2, 3 or 4-pyridyl, which pyridyl groups may optionally be substituted, or phenyl or substituted phenyl which substituents may be as described above;

A is —(CH$_2$)—$_n$ wherein n is 2,3 or —CH=CH—.

Compounds of each of the structures (I), (III), (IV) and (V) exist in solution at least partly as compounds of formula (I).

For example, recent evidence as described in Berners-Price et al. entitled "Self-assembly of silver (I) and gold (I) complexes of 1,2-bis(di(2-pyridyl)phosphino)ethane, Abstract for the RACI Inorganic Division Conference IC, Perth, Jul. 4–7 1994, shows that the compounds of formula (I) where R$_1$–R$_8$=2-pyridyl and (i) M=Au(I), and X=Cl— and (ii) M=Ag(I), and X=NO$_3^-$ do not actually have this structure in the solid state. These compounds actually have the dimeric structure shown as formula (III). This is very significant because only the formula I structure was shown in the EP0198696. The activity data reported for this compound in this reference and also in Berners-Price et al. (1990) above probably correspond to a compound of formula (III) where R=2-pyridyl, M=Au(I) and X=Cl$^-$.

In solution compounds of formula (III) are actually a mixture of compounds of formula (I), formula (III) and formula (IV).

Similarly, our recent evidence shows that the compound of formula (V) where R$_1$–R$_8$-3-pyridyl and A=(CH$_2$)$_2$ and X=Cl$^-$ exists in solution largely as the complex [Au(d$_3$pype)$_2$]$^+$ (formula I).

For details as to synthesis of ligands of formula (II), reference should be made to International Application No. PCT/AU95/00834—which disclosure is incorporated herein by reference.

EXPERIMENTAL

COMPLEXES OF d4pype

[i.e. 1,2-bis(di-4-pyridylphosphino)ethane]
METHOD 1—Using thiodyglycol

Thiodyglycol (0.07 g, 0.59 mmol) in acetone (1 ml) was added to sodium tetrachloroaurate(III) (0.1 g, 0.27 mmol) in water (3 ml) at 0° C. The colourless solution was then added dropwise over 5 min to an acetone (25 ml)/methanol (25 ml) solution of d4pype (0.22 g, 0.55 mmol). The addition resulted in a clear yellow solution.

The volume was reduced by rotary evaporation affording a yellow oil. The oil was precipitated with acetone. The precipitate was dissolved in ethanol filtered and hexane added until the solution became cloudy. A small volume of ethanol was added again until the cloudiness dissipated and the solution was stored in the freezer for 6 weeks, yielding a crystalline sample of [Au(d4pype)$_2$]Cl (i.e. a compound of formula (I) where R$_1$=R$_2$=R$_3$=R$_4$=R$_5$=R$_6$=R$_7$=R$_8$=4 pyridyl, M is Au(I), X is Cl⁻ and A is —(CH$_2$)$_2$—) $^{31}$P NMR:δ 22.5 (CD$_3$OD). This method is based on Berners-Price et al. (1990) above.

METHOD 2—using Au(CO)Cl

Au(CO)Cl (0.13 g, 0.5 mmol) was weighed into a flame-dried Argon tilled schlenk flask and 20 ml of dry, degassed THF was added. The resulting slurry was stirred and d4pype (0.4 g, 1.0 mmol) was added immediately in one quantity. The resulting off-white precipitate was collected by filtration—and recrystallised by dissolving the precipitate in methanol, filtering the methanol solution and reprecipitating the target compound with Et$_2$O (0.43 g, 85%)

[Ag (d4pype)$_2$] NO$_3$

AgNO$_3$ (0.084 g, 0.5 mmol) was added to a THF (20 ml) suspension of d4pype (0.4 g, 1.0 mmol). The reaction was stirred overnight and the product was collected by filtration. Recrystallisation by dissolving the crude material in methanol, filtering the methanol solution and re-precipitating with Et$_2$O afforded a pure white sample of the desired compound (0.2 g, 41%). This compound is a compound of formula (I) where M is Ag(I), all R groups are 4-pyridyl and X is nitrate ($^{31}$P NMR (D$_2$O) δ 2.1, J($^{31}$P-$^{107}$Ag)=232.5, Hz).

COMPLEXES OF d3pype

[i.e. 1,2-bis(di-3-pyridylphosphino)ethane]

[Au$_2$(d3pype)$_2$ Cl$_2$]

Au(CO)Cl (0.065 g, 0.25 mmol) was weighed into a flame dried Argon filled schlenk flask, and 20 ml of dry, degassed THF was added. The resulting slurry was stirred and d3pype (0.2 g, 0.5 mmol) was added immediately in one quantity. The resulting white precipitate was collected by filtration, and recrystallised from a (1:2) methanol-ether mixture yield (0.2 g, 82%). The compound isolated was a compound of formula (V) where all R groups are 3-pyridyl, M is Au(I), X is Cl⁻ and A is —(CH$_2$)$_2$—. In solution the compound dissociates to give a mixture containing [Au(d3pype)$_2$]Cl ($^{31}$P NMR (D$_2$O):δ 13.5).

[Au(d3pype)$_2$]Cl d3pype (0.4 g, 0.99 mmol) was dissolved in DMSO (20 mL) under an atomosphere of argon. Bu$_4$NAuCl$_2$ (0.236 g, 0.46 mmol was added as a solid and the resulting yellow solution was stirred overnight. In an attempt to precipitate the product Et$_2$O (10 mL) was added but no precipitate formed after several hours refrigeration, but instead the solution settled into two layers. To this mixture toluene (30 mL) was added and the clear pale yellow solution cooled to −20° C. for 24 hrs during which time the desired compound precipitated as a light yellow solid and was collected by filtration. Yield (0.3 g, 60%). $^{31}$P NMR (D$_2$O) δ 13.5. This compound is a compound of formula (I) where all R groups are 3-pyridyl, M is Au(I), X is chloride and A is —(CH$_2$)$_2$—.

[Ag(d3pype)$_2$]NO$_3$ d3pype (0.303 g, 0.75 mmol) was dissolved in acetone (40 ml) and AgNO$_3$ (0.061 g, 0.358 mmol) in H$_2$O (0.4 mL) added dropwise resulting in the immediate formation of a fine white suspension. The volume of solvent was concentrated to 20 mL and the flask cooled overnight at −20° C. The cold suspension was filtered affording the compound as a semi-crystalline solid. Yield 0.2 g, 57%. $^{31}$P NMR (D$_2$O) δ 4.3 ppm, J($^{31}$P-$^{107}$Ag) 237 Hz. This compound is a compound of formula (I) where all R groups are 3-pyridyl, M is Ag(I), X is nitrate and A is —(CH$_2$)$_2$—.

[Cu(d3pype)$_2$Cl d3pype (0.2 g, 0.5 mmol) was added to CuCl (0.0246 g, 0.25 mmol) in acetonitrile (20 mL) and the reaction was stirred overnight, affording a light yellow solid. The solid was collected by filtration and washed with cold acetonitrile (0.134 g, 60%). The compound isolated was that of formula (I) with all R groups being 3-pyridyl, M is Cu(I), X is Cl and A is —(CH$_2$)—. $^{31}$P NMR (CDCl$_3$):δ 14.3.

Complexes of d2pype

[i.e. 1,2-bis(di-2-pyridylphosphino)ethane]

[Au(d2pype)$_2$]$_2$(Cl)$_2$

METHOD A: Thiodiglycol (0.23 g, 1.9 mmol) in acetone (1 mL) was added to sodium tetrachloroaurate(III) (0.18 g, 0.497 mmol) in water (3 mL) at 0° C. The solution was stirred until it became colourless. The colourless solution was then added dropwise over 5 minutes to an acetone suspension (60 mL) of 1,2-bis(di-2-pyridylphosphino) ethane (0.4 g, 0.99 mmol). This addition resulted in the formation of a clear yellow solution, however, after 5 minutes of stirring at room temperature, a yellow solid precipitated. The solution was stirred for 1 hour, and the solid was then collected by filtration. The solid was dissolved in ethanol, filtered and precipitated by the addition of an equivalent volume of hexane, yielding a yellow solid [Au(d$_2$pype)$_2$]$_2$(Cl)$_2$ (0.41 g, 80%, mp 254–255° C.). This is a compound of formula (III) wherein all R groups are 2-pyridyl, M is Au(I), X is Cl⁻. The dimeric structure in the solid state was confirmed by X-ray crystallography. $^{31}$P NMR shows that in solution (e.g. CD$_3$OD) the compound exists as a mixture of [Au(d2pype)$_2$]⁺(δ 26.8), [Au(d2pype)$_2$]$_2$$^{2+}$ (δ 18.8 and 25.2) and [Au(d2pype)$_2$]$_3$$^{3+}$ (δ 16.0, 18.5, 25.2).

METHOD B: Addition of 1,2 bis(di-2-pyridylphosphino) ethane to 1,2-bis(di-2-pyridylphosphino)ethane]bis (chlorogold).

1,2-bis(bi-2-pyridylphosphino)ethane]bis(chlorogold) (0.01 g, 0.012 mmol) was dissolved in DMF (2 ml). Addition of 3 equivalents of 1,2 bis(di-2-pyridylphosphino)ethane (0.014 g, 0.035 mmol) resulted in complete conversion (100%) to the title compound [Au(d$_2$pype)$_2$]$_2$Cl$_2$.

Preparation of [Ag(d2pype)$_2$]$_2$ (NO$_3$)$_2$ 1,2-bis(di-2-pyridylphosphino)ethane (0.4 g, 0.99 mmol) was suspended in acetone (20 mL) and AgNO$_3$ (0.077 g, 0.453 mmol) in H$_2$O (1 mL) added. The solution was stirred at room temperature, with almost immediate formation of a clear solution. The solution was stirred for a further hour, and the solvent allowed to evaporate at room temperature. The product [Ag(d2pype)$_2$]$_2$(NO$_3$)$_2$, solidified as white crystals (0.83 g, 94%, mp 277–287° C.). This compound was a compound of formula (III) wherein all R groups are -2-pyridyl, M is Ag(I), A is —(CH$_2$)$_2$— and X is NO$_3$⁻. The dimeric structure in the solid state was confirmed by X-ray crystallography. $^{31}$P NMR shows that in solution (e.g. CD$_3$OD) the compound exists as a mixture of [Ag(d2pype) $_2$]⁺ (δ 10.5), [Ag(d2pype)$_2$]$_2$$^{2+}$ (δ 6.4 and 15.5) and [Ag (d2pype)$_2$]$_3$$^{3+}$ (δ 4.0, 9.5 and 18.9).

Preparation of [Cu(d2pype)$_2$]$_2$(Cl)$_2$ d2pype (0.2 g, 0.5 mmol) was added to CuCl (0.0246 g, 0.25 mmol) in CH$_3$CN (20 mL) and the reaction was stirred overnight, affording a fine yellow suspension. The solvent was removed in vacuo and the remaining solid was recrystallised from acetonitrile (0.15 g, 61%). This compound is a formula (III) compound where all R groups are -2-pyridyl, M is Cu(I), X is Cl⁻ and A is —(CH$_2$)$_2$⁻. The dimeric structure in the solid state was confirmed by X-ray crystallography.

COMPLEXES OF 2-pyppe (i.e 1,(di-2-pyridylphosphino)-(diphenylphosphino) ethane

[Au(2-pyppe)$_2$]Cl 2-pyppe (0.3 g, 0.75 mmol) was dissolved in acetone (25 mL) under an argon atmosphere. To this clear solution, Bu$_1$NAuCl$_2$ (0.187 g, 0.37 mmol) was added. The resulting clear colourless solution was stirred for 4 hours, during which time the product formed as a white precipitate and was collected by filtration. Yield (0.24 g, 63%). $^{31}$P NMR (CD$_3$OD) δ 25.5 (multiplet). This compound is a compound of formula I where R$_1$=R$_3$=Ph and R$_2$=R$_4$=2-pyridyl, M is Au(I), X is chloride and A is —(CH$_2$)$_2$—.

Determination of Cell Survival After Drug Treatment

In FIGS. 1–4 and Table 1, reference is made to the cell lines HeLa, HeLa-S1a, JAM, CI-80-13S and MM96.

The origins of the human melanoma cell line MM96 has been described in Whitehead et al., 1973, Pigment Cell 1 383–389. The cell line JAM is described in Ward et al., 1987, Cancer Res. 47 2662–2667. The origin of the ovarian tumour line CI-80-13S has been described in Bertoncello et al., 1985, Aust. J. Exp. Biol. Med. Sci. 63 241–243. The origin of the cervical carcinoma cell line HeLa has been described in Maynard et al., 1986, Cancer Res. 46 5009–5093. The subclone HeLa-S1a was derived by stably transfecting HeLa with PAI-2 cDNA described in Schleuning et al., 1987, Mol. Cell. Biol. 7 4564–4567 in the sense orientation under the control of the cyto-megalovirus (CMV) promoter. The stably infected subclone was isolated following G418 selection and expression of the PAI-2 transgene characterised by immunoblot analysis and quantitated by ELISA. All of these cell lines have been used before for carrying out cell survival assays referred to in FIGS. 1–4. Cells were cultured at 37° in 5% CO$_2$/air in Roswell Park Memorial Institute medium 1640 containing 5% foetal calf serum, 100 μg/ml streptomycin, 100 IU/ml penicillin, 1 mM pyruvate, 50 μM nicotinamide and 3 mM HEPES.

Cells were seeded in microtitre plates (lowest number for fastest growing cells: 1000 HeLa, 2000 MM96, 3000 and CI-80-13S cells per 6 mm well in 100 μl), normally but not necessarily allowed to attach overnight, then 5 dilutions of the drug were added to duplicate wells. After an overnight incubation to equilibrate the pH, the lids were quickly taped around the edge to prevent evaporation. The plates were incubated for 5–7 days, until the controls were nearly confluent. Cell growth/morphology was scored at each dose visually (inverted microscope). The medium was then replaced by 50 μl fresh medium containing 2 u/Ci/ml [methyl-3H]-thymidine (5 Ci/mmol; Radiochemical Centre, Amersham, Bucks., U.K.) and incubated for 2–4 hr. The cells were washed with PBS (0.1 M NaCl, 50 mM phosphate, pH 7.2), detached with 100 μl of PBS containing 0.2 mg/ml trypsin and 10 mM EDTA, and washed onto a glass fibre GF/a filter mat with water using a cell harvester. Later, wells were checked under the microscope to ensure complete detachment and washout. Radioactivity was determined in an LKB Beta Plate counter and the results plotted as log % control cpm versus dose. The ID$_{50}$ (dose required to give 50% survival) was interpolated from this survival curve.

We have tested the 4-pyridyl complex, where R$_1$ through R$_8$ is 4-pyridyl and M=Au(I), A=(CH$_2$)$_2$ and X=Cl$^-$ against four human tumour cell lines: (i) MM96 melanoma, (ii) HeLa cervical carcinoma, (iii) CI-80-13S ovarian and (iv) HeLa-Sla.

The data (FIG. 1) shows that this complex is inactive against MM96 melanoma and HeLa cervical carcinoma in vitro, and selectively cytotoxic against CI-80-13S ovarian and HeLa-S1a.

We have tested the 3-pyridyl complex of formula (V) where R$_1$ through R$_8$ is 3-pyridyl and, where M=Au(I), A=—(CH$_2$)—$_2$ and X=Cl$^-$ against four human tumour cell lines: (i) MM96 melanoma, (ii) HeLa cervical carcinoma, (iii) CI-80-13S ovarian and (iv) HeLa-S1a.

The data (FIG. 2) shows that this complex is inactive against MM96 melanoma and HeLa cervical carcinoma in vitro, and selectively cytotoxic against CI-80-13S ovarian and HeLa-S1a.

We have tested the following compounds of formula (III) against the four human tumour cell lines described above, i.e.:

(a) where M=Au(I), X=Cl$^-$ and R$_1$ through R$_8$ is 2-pyridyl; and (b) where M=Ag(I), X=NO$_3^-$ and R$_1$ through R$_8$ is 2-pyridyl.

Figure 1:
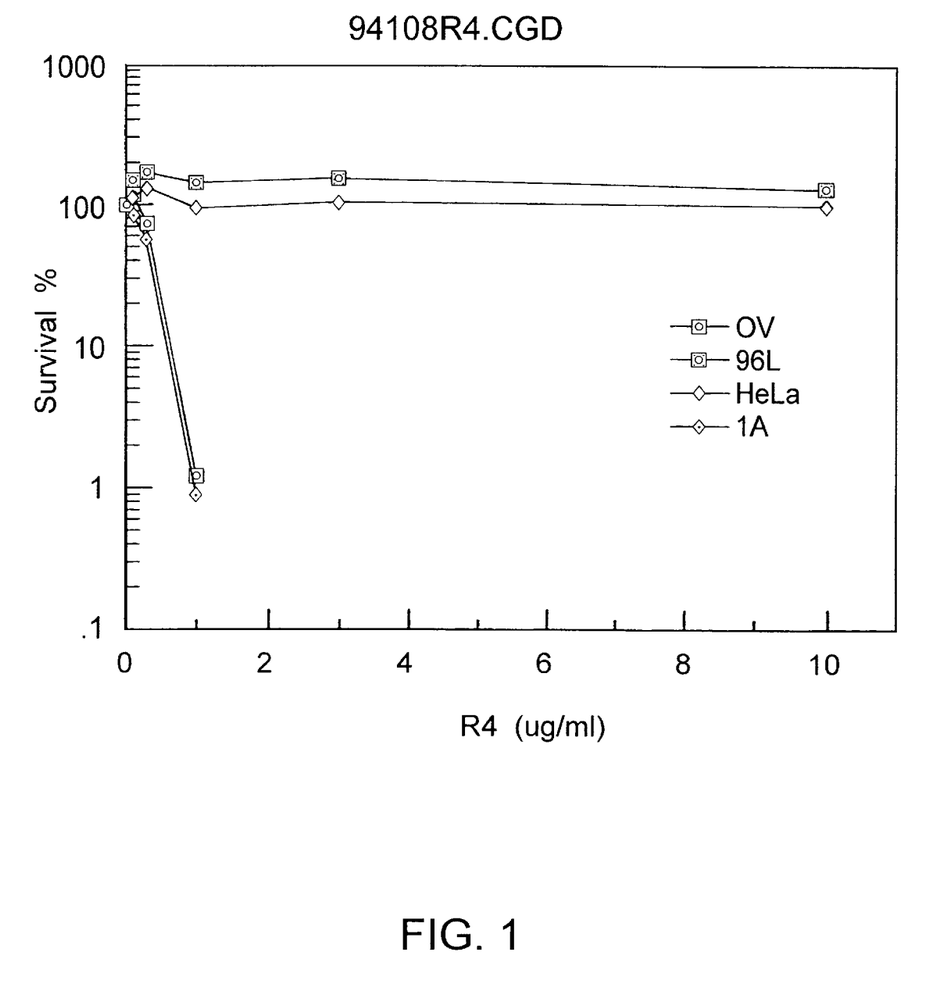
Figure 2:
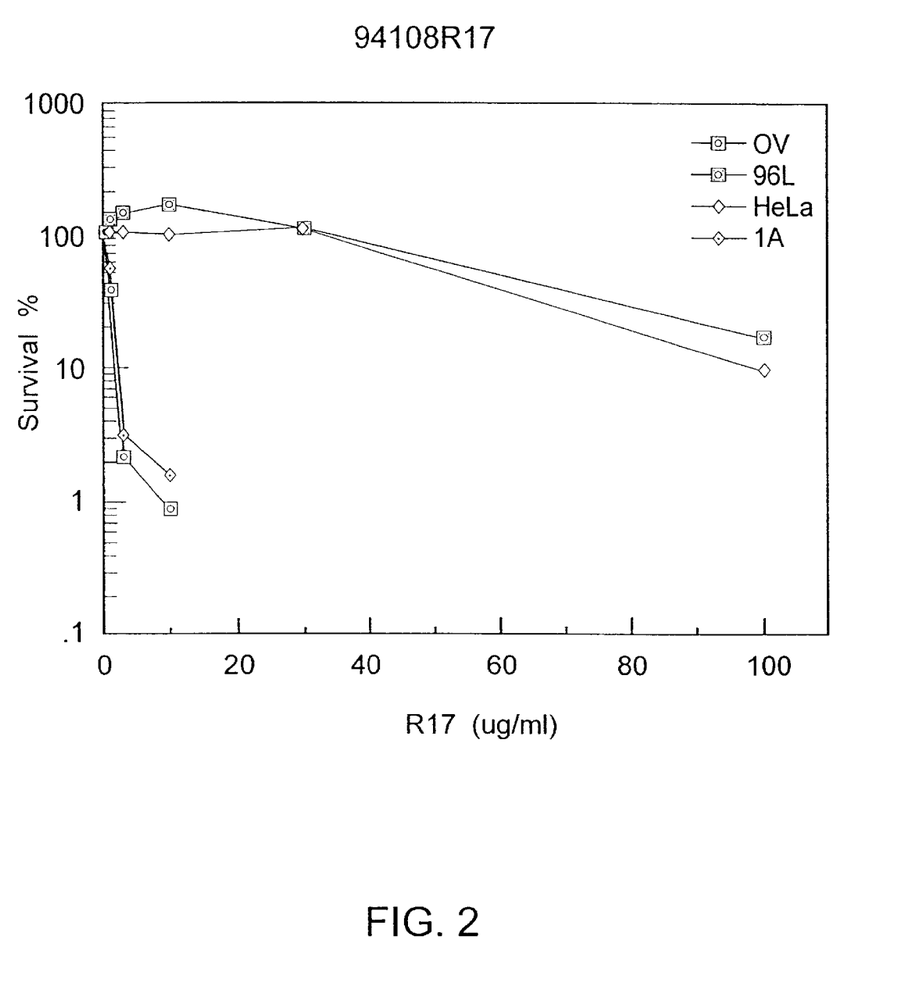
Figure 3:
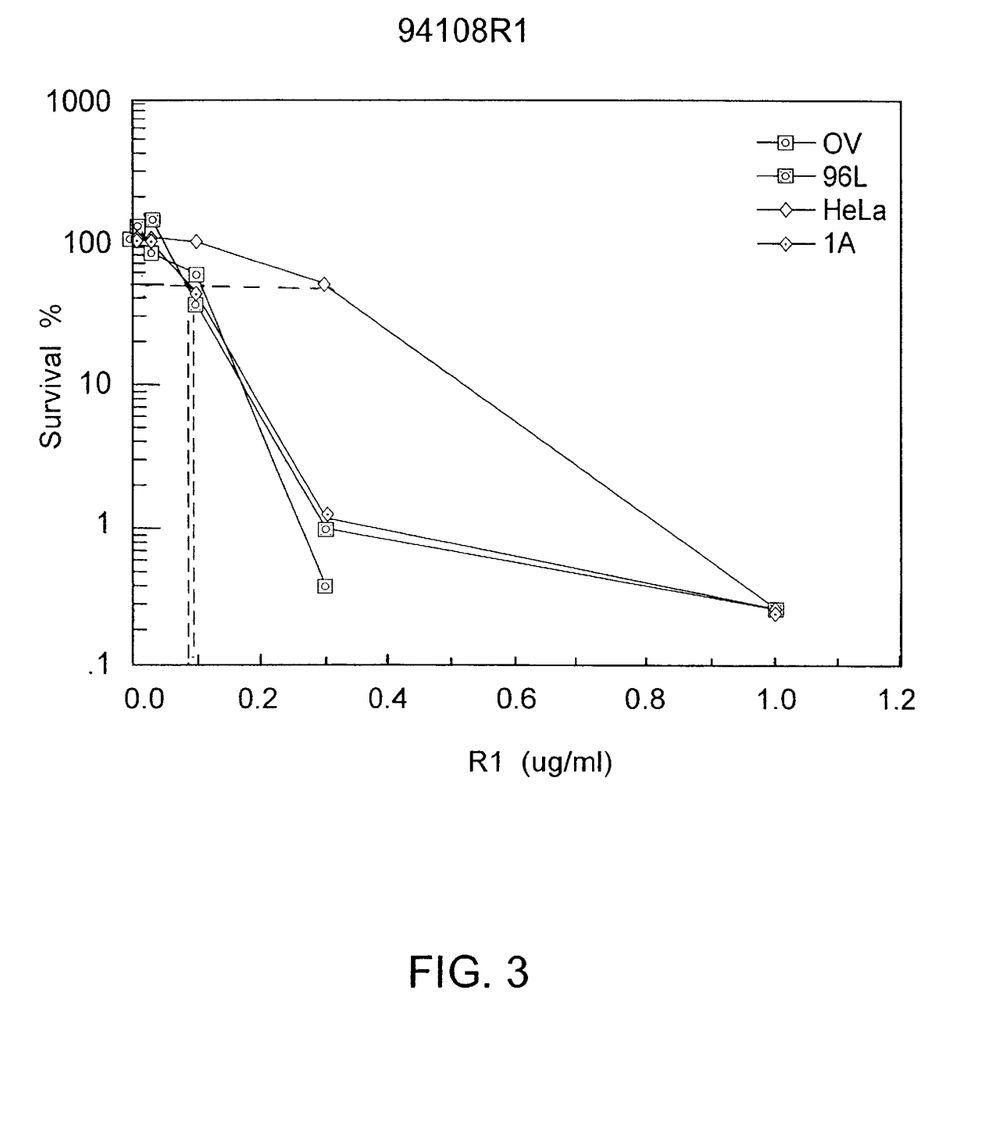
Figure 4:
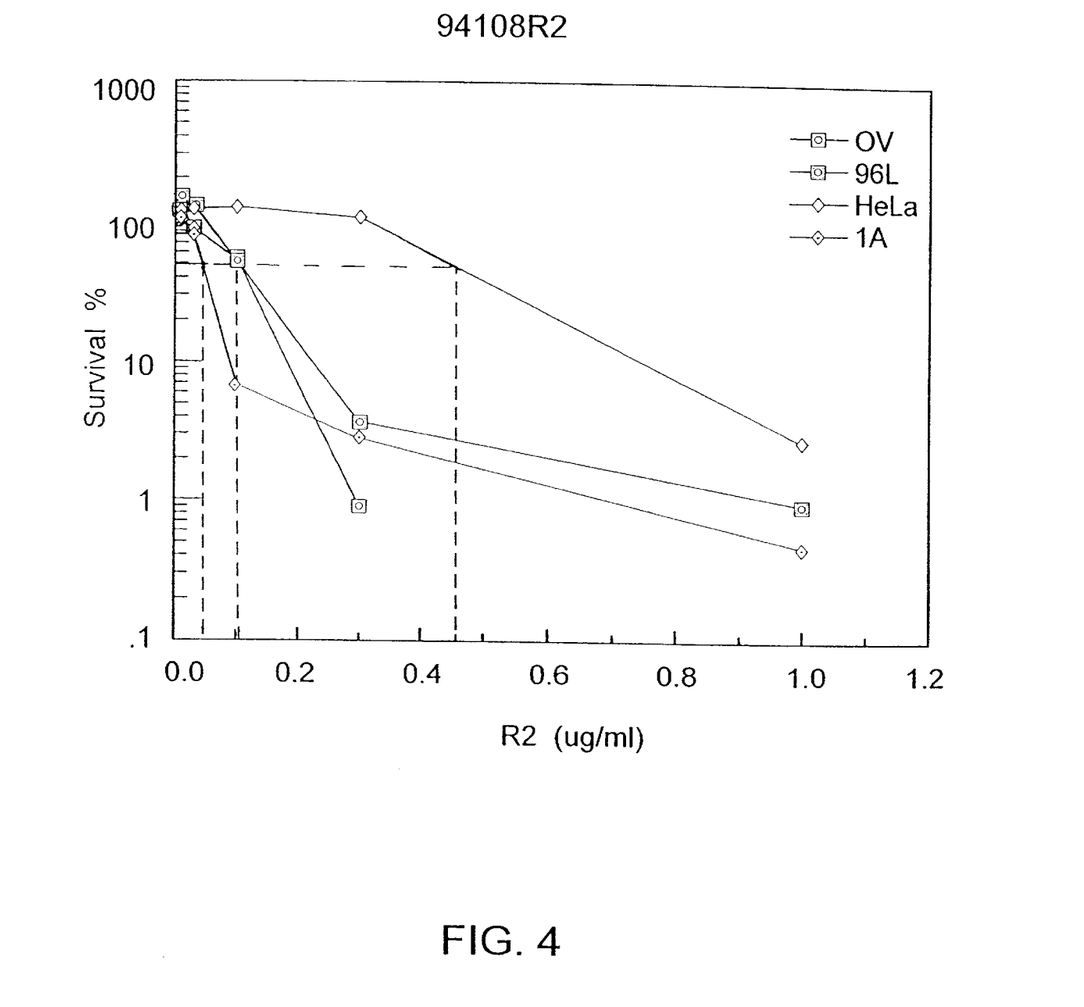
Figure 5A:
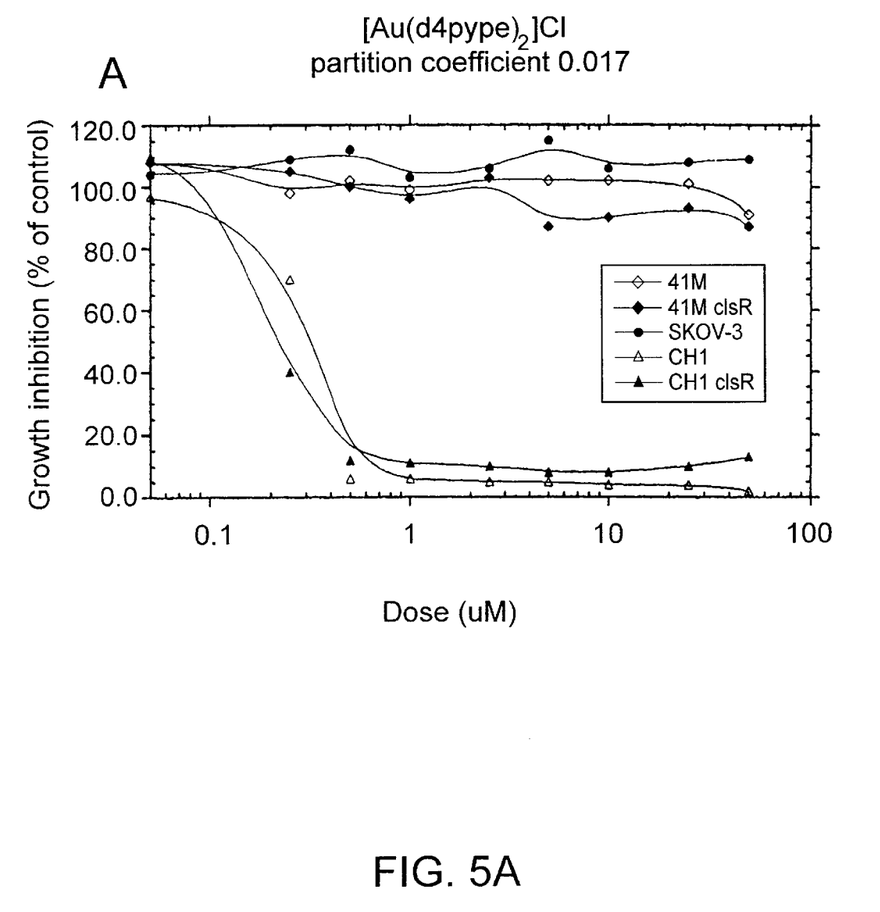
Figure 5B:
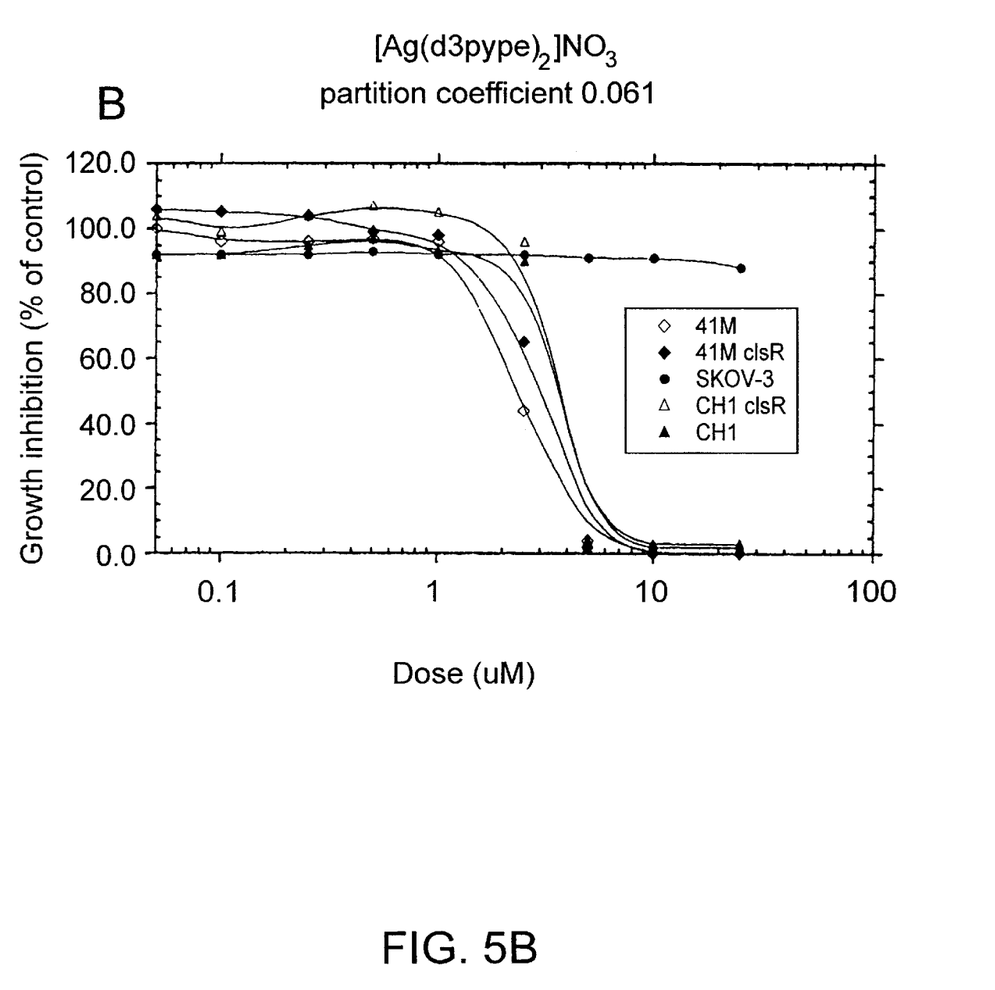
Figure 5C:
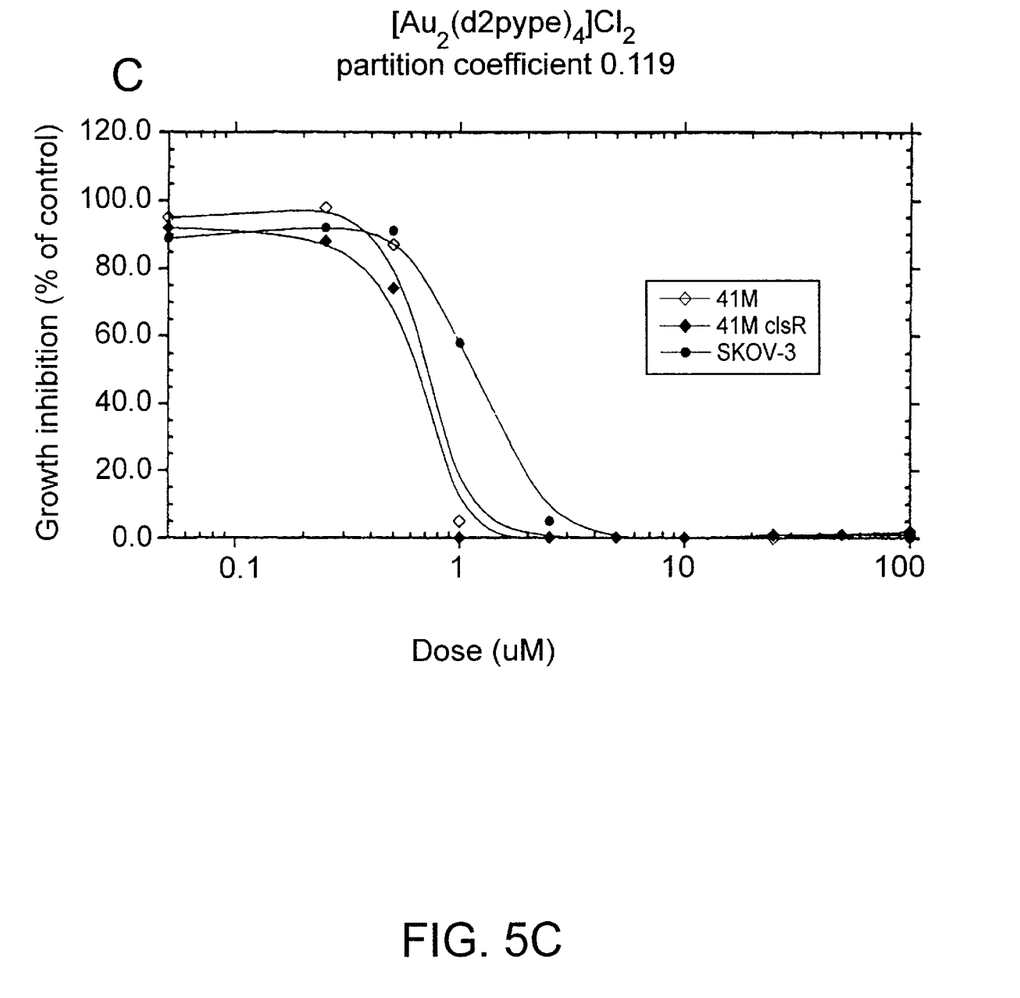
Figure 5D:
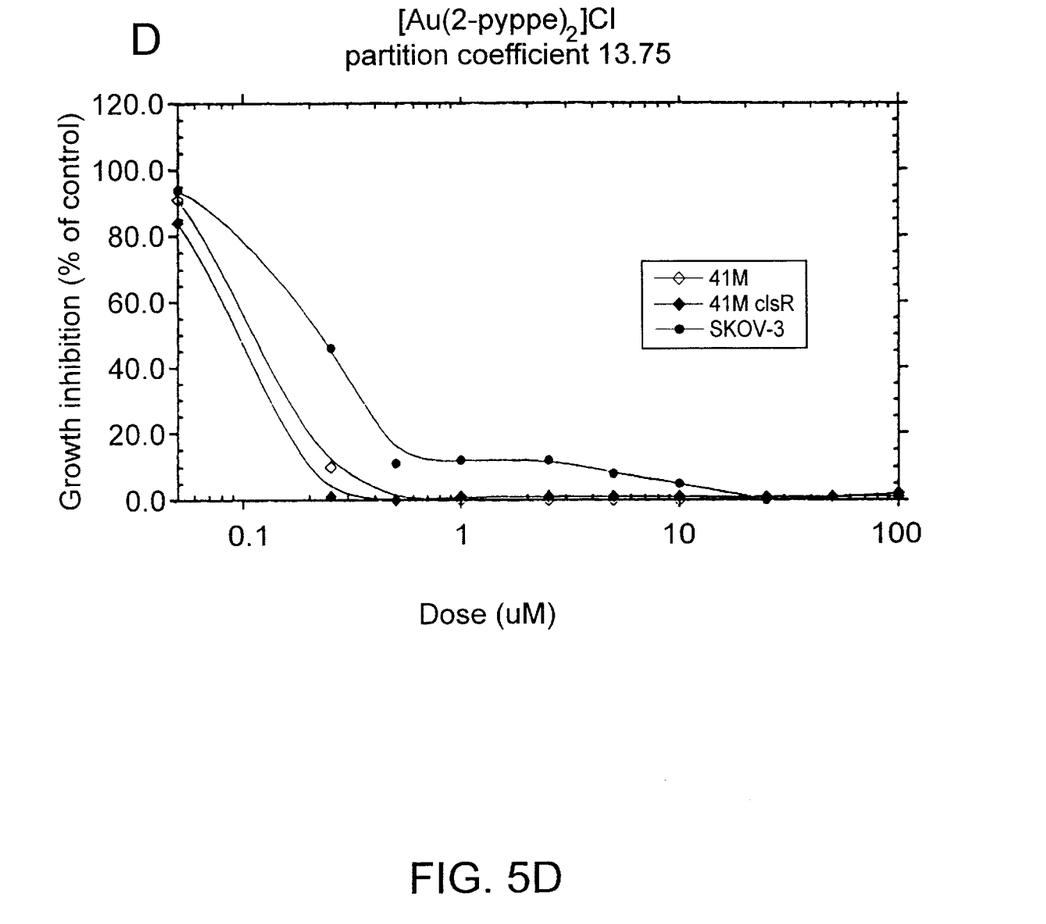

These compounds are all cytotoxic against all four cell lines. The data for the Au(I) and Ag(I) complexes are shown in FIGS. 3 and 4. These show that these compounds are cytotoxic to all four cell lines. They do not show the same selectivity against the cisplatin-resistant lines as the compounds of formula (I) or (V) where R=4-pyridyl and 3-pyridyl.

Determination of Cell Survival in Cisplatin Sensitive and Resistant Cell Lines In Table 2, reference is made to cell lines 41M, 41M-cisR, SKOV-3, CH1 and CH1-cisR.

The sensitive CH1 cell line was established from a patient with drug-sensitive disease and its resistant variant (CH1-cisR) was generated by prolonged in vitro exposure to cisplatin during which it acquired more efficient DNA repair as described in Kelland et al., 1992, Cancer Research 52 3857–3864. The sensitive 41M cell line was also established from a patient with a sensitive tumor and its resistant variant (41M-cisR) was generated in the same way but acquired decreased uptake across the cell membrane (Kelland et al., 1992, supra). The intrinsically-resistant SKOV-3 ovarian carcinoma cell line has high glutathione levels as described in Mistry et al., 1991, Brit. J. Cancer 64 215–220 and reduced levels of bi-functional cisplatin-DNA lesions as described in McKeage et al., 1994, Brit. J. Cancer 69 1–7. The characteristics of the cell line pairs CH1/CH1 cisR, 41M/41McisR and 41M/SKOV3 are described in Table 3.

The cytotoxicity assay used sulforhodamine B which stains the basic amino acids. Cells (5000 or 2500 for SKOV-3) were seeded into 96 well microtitre plates (Linbro, Flow Laboratories Inc., USA) in 0.1 ml of medium. After an overnight incubation, the metal phosphine compounds were dissolved in 0.9% NaCl or ethanol and diluted with medium, were added at concentrations ranging from 0.005 to 50 μM to quadruplicate wells. After 96 hrs incubation, the medium was removed and cells were fixed in 0.2 ml of cold 10% (w/v) trichloroacetic acid (May & Baker Ltd., Dagenham, England) for 30 mins at 4° C. The plates were washed five times with tap water. Then 0.1 ml of 0.4% (w/v) sulforhodamine B (Sigma Chemical Co., St. Louis, USA) dissolved in 1% acetic acid (Ajax Chemicals, Australia) was added to the wells and left to stand at room temperature for 15 mins. The plates were then washed five times with 1% acetic acid and left to dry overnight. The next morning, 0.1 ml of 10 mM Tris buffer (Sigma Chemical Co., St. Louis, USA) was then added to each plate to solubilise the dye. Absorbance was read at a wavelength of 570 nm using a 96 well plate reader Dynatech MR 5000 plate reader. Absorbance of treatment cells was expressed as a percentage of positive (drug-free) controls. The results were plotted as percentage growth versus drug concentration. The drug concentration resulting in a 50% growth inhibition was termed the $IC_{50}$. The passage numbers used for the cytotoxicity assay from each cell line were, CH1 passages 50–58, CH1 cis-R passages 77–83, 41M passages 50–63, 41M cisR 81–92 and SKOV-3 passages 106–128.

Relationship of Cytotoxicity and Selectivity to Partition Co-efficients

The severe and unacceptable hepatotoxicity of the parent compound $[Au(dppe)_2]^+$ has been attributed to the lipophilic cationic properties of the complex which promotes its non-selective uptake and inhibition of mitochondrial function in normal cells. Our original hypothesis as described in Berners-Price et al., Synthesis and Structural Studies of Pyridyl Phosphine Complexes: Potential Anti-tumour Drugs Abstract for the 9th National Conference of the Royal Australian Chemical Institute, Melbourne, Australia, December 1992, was that by reducing the lipophilicity of the parent compound $[Au(dppe)_2]^+$, it may be possible to retain anti-tumour activity without disrupting mitochondrial function.

The data in Table 1 and Table 2 show that by exchanging some or all of the eight phenyl substituents in the parent complex $[Au(dppe)_2]^{30}$, by 2-, 3- or 4-pyridyl substituents, it is possible to fine-tune the lipophilic/hydrophilic nature of the compounds within a range of octanol/water partition co-efficients between 0.01 and 25.5. Analogs containing Ag(I) or Cu(I) in place of Au(I) also fall in this range.

The data shown in Tables 1 and 2 show that within the range of partition co-efficients 0.01–25.5, and more particularly within the measured range of 0.01–14, there is a difference in the degree of selectivity of the compounds for inhibiting the growth of different human tumour cell lines grown in culture.

The most lipophilic compounds (e.g. $[Au(2-pyppe)_2]Cl$ and $[Au(dppe)_2]Cl$) exhibit the least selectivity (i.e. they are cytotoxic to all the cell lines evaluated). The least lipophilic compound, $[Au(d4pype)_2]Cl$, exhibits the greatest selectivity being cytotoxic to only four of the nine cell-lines tested.

This supports the hypothesis that the selectivity may be due to the preferential uptake of the compounds into mitochondria in these cells and that mitochondria may be key targets in the mechanism of action. It is known that a variety of lipophilic cations with delocalised charges (e.g. Rhodamine-123) accumulate in the mitochondria of most carcinoma derived cells more rapidly than in most untransformed cells and this has been attributed to the abnormally high mitochondrial membrane potentials characteristic of most carcinoma-derived cells. This has been described in Davis et al., 1985, J. Biol. Chem. 260 13844–13850 and Davis et al., 1988, Annual Review of Cellular Biology 4 155.

The work of Rideout et al., 1989, Anti-Cancer Drug Design 4 265–280 has shown that another class of lipophilic cations, phosphonium salts, selectively inhibited the growth of cultured carcinoma cells (human pancreatic carcinoma-derived cells PaCa-2) and Ehrlich Lettre Ascites cells (ELA) when compared with untransformed kidney epithelial cells. They attributed the basis for the selectivity to the abnormally high membrane potentials in carcinoma cells. They observed that selective inhibition of PaCa-2 growth relative to CV-1 was optimal for compounds falling in narrow range of octanol/water partition co-efficients (between 0.013 and 0.24). They proposed that the relationship between partition co-efficients and cytostatic selectivity suggested that rates of diffusion across cytoplasmic and mitochondrial membranes are key factors in structure anti-carcinoma selectivity relationship. Very hydrophobic and very hydrophilic compounds are poorly selective due to slow penetration through the cytoplasmic membrane into the cytoplasm. Between these extremes uptake is sensitive to the membrane potential.

Consideration of the results in Tables 1 and 2 with regard to these other studies now suggest that our original hypothesis was incorrect. Less lipophilic compounds retain anti-tumour activity and the mechanism appears to involve disruption of mitochondrial function, in complete contrast to what we had initially proposed. It is anticipated that compounds within the range of partition co-efficients 0.01–25 and more particularly within the measured range of partition co-efficients (0.01–14) will have an improved selectivity compared to the parent compound $[Au(dppe)_2]^+$ and therefore are of clinical potential.

Another important feature highlighted by the data shown in Tables 1 and 2 is that compounds within the range of partition co-efficients 0.01–25 demonstrate cytotoxicity against cisplatin-resistant cell lines. Selectivity is optimal for compounds in the range 0.01–0.12. In addition, in several cases the cisplatin-resistant cell lines are more sensitive to the pyridyl diphosphine metal co-ordination compounds than non-resistant cells. For example, compare the cytotoyic potency of $[Au(d2pype)_4]Cl_2$ in the intrinsically cisplatin-resistant ovarian carcinoma CI80-13-S compared to the non-resistant ovarian carcinoma JAM and in the cisplatin-sensitive HeLa compared to the cisplatin-resistant sub-clone HeLaS1a. Similarly, the cisplatin-resistant ovarian carcinomas 41M-cisR and CH1-cisR were consistently more sensitive to $[Au_2(d3pype)_2Cl_2]$ than were the non-resistant 41M and CH1 cell lines. Compounds of this class therefore offer great clinical potential for treatment of cisplatin-resistant tumours. It is notable that these compounds are able to overcome different mechanisms of cisplatin resistance: increased DNA repair (CH1-cisR), reduced transport (41M-cisR) and increased cellular glutathione (SKOV-3).

Other researchers have proposed, that combinations of cisplatin and mitochondrial agents may be a useful therapeutic strategy for attacking cisplatin resistant tumours and increasing body of recent evidence suggest that mitochondria may play a key role in determining cisplatin sensitivity in tumour cells. For example, a number of agents reported to potentiate cisplatin sensitivity are known to have significant effects on mitochondria (Andrews et al., 1992, Cancer Research 52 1895–1901). Combination chemotherapy using cisplatin and agents that alter mitochondrial function (including the lipophilic cation delqualinium) have been shown to enhance cisplatin cytotoxicity in vitro (Singh and Moorehead, 1992, Int. J. Oncol. 1 825–829) and in vivo (Christman et al., 1990, Gynecol. Oncol. 39 72–79) and Rhodamine 123 uptake increases in cells treated with cisplatin (Shinomiya et al., 1992, Exp. Cell Research 198 159–163). A platinum (II) rhodamine complex ($PtCl_4$ $(Rh123)_2$) is effective against cisplatin-resistant tumours (Ara et al., 1994, Cancer Research 54 1497–1502).

Studies by Andrews et al., 1992, above have established that the cisplatin-resistant 2008 human ovarian cells (C13*) have an elevated mitochondrial membrane potential and the mitochondria are morphologiclally deranged and the cells are sensitive to lipophilic cations. By selecting cells resistant to Rh123 the cisplatin resistance was lost, demonstrating that the elevated mitochondrial potential is central to the expression of resistance to cisplatin in these cells (Zinkewich-Peotti and Andrews, 1992, 52 1902–1906). Similarly, mitochondrial alterations were reported to be an important component of the resistance mechanism in two other human tumour cell lines with acquired cisplatin resistance (SCC-25) squamous cell carcinoma and MCF-7 breast carcinoma) (Ara et al., 1994 above) and a photofrin-induced photodynamic therapy-resistant variant of a radiation-induced fibrosarcoma-1 cell line which is cross-resistant to cisplatin (Moorehead et al., 1994, Cancer Research 54 2556–2559).

For the cell lines HeLa-S1a and CI-80-13S, it has been established that cisplatin resistance is associated with mitochondrial defects (Dong et al., submitted for publication). For the pairs 41M/41M-cisR and CH1/CH1-cisR, the results in Table 1 show that the cisplatin resistant cells are more sensitive to Rhodamine than the nonresistant cells, consistent with an elevated mitochondrial potential.

In FIG. 5, reference is made to growth inhibition of human ovarian cancer cell-lines after a 96h incubation with selected pyridyl diphosphine metal coordination complexes, demonstrating the relationship between octanol/water partition co-efficient and the degree of selectivity and cytotoxic potency. The least lipophilic complex [Au(d4pype)$_2$]Cl (A) exhibits the greatest selectivity killing only the CH1/CH1 cisR pair. Increasing the lipophilicity as in [Ag(d3pype)$_2$]NO$_3$ (B) improves activity in the 41M pair while retaining activity against the CH1 cell-lines, but SKOV-3 is resistant. [Au$_2$(d2pype)$_4$]Cl$_2$ (C) and [Au(2-pyppe)$_2$]Cl (D) are cytotoxic to the 41M pair and the resistant SKOV-3, with the degree of potency increasing with the increase in lipophilicity. The pattern of activity of the pyridyl diphosphine complexes in these cell lines is dissimilar to that of cisplatin suggesting a mode of action different to that of platinum-based drugs.

In summary, the pyridyl diphosphine metal co-ordination compounds offer several important advantages over existing anti-cancer drugs used clinically. By targetting mitochrondia, they may act by a different mechanism of action and the differences in the membrane potentials of carcinoma and normal cells provides a mechanism for selective toxicity. Interaction with different biological targets provides a rationale for treatment of drug-resistant tumour cells, as demonstrated for cisplatin resistant cells. The different mechanism of action offers the potential to extend the spectrum of clinically responsive tumours and to allow combination chemotherapy with non-overlapping side effects.

In Table 1, JAM and CI-80-13S are ovarian tumours, HeLa is a cervical tumour and MM96 is a melanoma In Table 2, all the tumours are ovarian tumours. We have very preliminary data for [Au(d4pype)$_2$]Cl against a cisplatin sensitive lung tumour PC9 showing modest activity. Thus for PC9, the IC$_{50}$ is 25 $\mu$M. In this regard, PC9 is a lung tumour and its derivation is discussed in Hong et al., 1993, Cancer Research 53 3302–3307 and Bungo et al., 1990, Cancer Research 50 2549–2553. Therefore, we have demonstrated utility against ovarian, cervical and lung tumours as well as melanoma.

Previous anti-tumour evaluation of metal phosphine compounds (e.g. those in EP0164970) was confined to murine tumours whose value in predicting clinical activity is in doubt (Harrap, K. R., 1983, In: Cancer Chemotherapy; F. M. Muggia, Ed.; Martinus Nijhoff, pp 171–217). In contrast, all the activity data disclosed here relates to human tumours. In particular, the activity assays used for the human tumour cell-lines in Table 2 correctly predicted the clinical activity of both cisplatin and the Pt(IV) ammine/amine carboxylate complex JM216 (Hills et al., 1989, Brit. J. Cancer 59 527–534; McKeage et al., 1995, Cancer Chemother. Pharmacol. 36 451–458 and Kelland et al., 1993, Cancer Research 53 2581).

The pharmaceutical compositions of this invention comprise an effective tumour cell growth-inhibiting amount of a therapeutic compound of the invention and an inert pharmaceutically acceptable carrier or diluent. These compositions are prepared in dosage unit form appropriate for parenteral administration which includes intravenous (i.v) or intra-peritoneal (i.p.) routes.

As the compounds are lipophilic, an oral route is also possible, as has been shown for the Pt(IV) ammine/amine carboxylate complex JM216. The platinum compound carboplatin is administered via an i.v. route. For ovarian cancers, an i.p. route may be most suitable.

Compositions according to the invention for parenteral administration include sterile aqueous or non-aqueous solutions, suspensions or emulsions. The composition may be in the form of a solution of the active ingredient in a minimal volume of dimethylacetamide or ethanol, for example 5% v/v, brought up to volume with peanut oil or normal saline solution. Polyethcxylated castor oil, for example 2 to 5% v/v, may also be used to solubilize the active ingredient. In addition, the composition may be in the form of a slurry with, for example, hydroxypropyl cellulose or other suitable suspending agent. As an emulsifying agent, lecithin for example may be used. The composition may also be provided in the form of a sterile solid which can be dissolved in a sterile injectable medium immediately before use.

In regard to pharmaceutical compositions, a preferred composition for oral administration is formulated as dry filled hard gelatin capsules.

It will be appreciated that the actual preferred dosages of the compounds used in the compositions of this invention will vary according to the particular complex being used, the particular composition formulated, the mode of administration and the particular site, host and disease being treated. The route of internal administration should be selected to ensure that an effective tumour cell growth inhibiting-amount of the metal complex contacts the tumour. Optimal dosages for a given set of conditions can be ascertained by those skilled in the art using conventional dosage determination tests in view of the above experimental data.

For oral administration, suitable dose ranges of 10 mg to about 150 mg/m$^2$ of body surface per day, for one to five days, repeated about every fourth week for about four courses of treatment (for example, the orally active platinum compound JM216, a suitable dose range is 30–120 mg/m2 per day for five days, repeated every fourth week (McKeage et al., 1995, Cancer Chemother. Pharmacol. 36 451–458)). For parenteral administration, the dose range generally employed is about 5 mg to about 50 mg/m$^2$ of body surface per day, for one to five days, repeated about every fourth week for about four courses of treatment.

The method for inhibiting the growth of tumour cells sensitive to a compound in accordance with this invention comprises administering to a host animal afflicted with said tumour cells, an effective tumour cell growth-inhibiting amount of the compound. As described above, during the course of treatment the active ingredient may be administered orally or parenterally in an amount selected from about 50 mg to about 1000 mg.

TABLE 1

Partition co-efficients and cytotoxicity data for pyridyl disphosphine metal co-ordination complexes' in certain human carcinoma cell lines in comparison to cisplatin and Rhodamine

| Compound | Partition co-efficient[a] | $IC_{50}$ ($\mu M$)[b] | | | | |
|---|---|---|---|---|---|---|
| | | HeLa | HeLa-S1a | JAM | C1-80-135 | MM96L |
| [Au(d4pype)$_2$]Cl | 0.017 | >10 (1) | 0.3 (1) | n | 0.32 ± 0.15 (3) | >10 (1) |
| [Au$_2$(d3pype)$_2$Cl$_2$][c] | n | 38 (1) | 0.4 (1) | n | 0.4 (1) | 56 (1) |
| [Au$_2$(d2pype)$_4$]Cl$_2$[c] | 0.119 | 0.24 ± 0.10 (3) | 0.06 ± 0.03 (3) | 0.10, 0.39 (2) | 0.06 ± 0.03 (3) | 0.09 (1) |
| [Ag$_2$(d2pype)$_4$](NO$_3$)$_2$[d] | 0.178 | 0.45 (1) | 0.05 (1) | n | 0.1 (1) | 0.1 (1) |
| [Au(dppe)$_2$]Cl | 25.41 | 0.95 ± 0.13 (3)[f] | 0.073 ± 0.005 (3)[f] | 0.73 ± 0.15 (3)[f] | 0.20 ± 0.03 (3)[f] | n |
| Rhodamine | 0.34[a] | 2.73 ± 0.28 (4)[f] | 0.58 ± 0.08 (3)[f] | 0.90 ± 0.03 (3)[f] | 0.105 ± 0.026 (3)[f] | n |
| Cisplatin | | 0.29 ± 0.04 (3)[f] | 0.62 ± 0.08 (3)[f] | 0.83 ± 0.3 (6)[f] | 4.17 ± 0.5 (g)[f] | n |

TABLE 2

Partition co-efficients and cytotoxicity data for pyridyl disphosphine metal co-ordination complexes in human ovarian carcinoma cell lines in comparison to cisplatin and Rhodamine

| Compound | Partition co-efficient[3] | $IC_{50}$ ($\mu M$)[b] | | | | |
|---|---|---|---|---|---|---|
| | | 41M | 41M-cisR | SKOV-3 | CH1 | CH1-cisR |
| [Au(d4pype)$_2$]Cl | 0.017 | >100 (4) | >100 (3) | >100 (4) | 0.4 ± 0.1 (4) | 0.6 ± 0.2 (4) |
| [Au$_2$(d3pype)$_2$Cl$_2$][c] | n | 70 ± 12 (4) | 47 ± 9 (3) | 71 ± 12 (4) | 0.9 ± 0.4 (3) | 0.5 ± 0.1 (3) |
| [Au(d3pype)$_2$]Cl | 0.035 | >25 (1) | 11 (1) | >25 (1) | 1.5 (1) | 10 (1) |
| [Ag(d4pype)$_2$]NO$_3$ | 0.035 | 1.5, 0,9 (2) | 0.7, 1.2 (2) | >100 (2) | 30 (1) | n |
| [Cu(d3pype)$_2$]Cl | 0.057 | >50 (1) | 30 (1) | >50 (1) | 3 (1) | n |
| [Ag(d3pype)$_2$]NO$_3$ | 0.061 | 2.0 (1) | 3.0 (1) | >25 (1) | 3.1 (1) | 3.1 (1) |
| [Au$_2$(d2pype)$_4$]Cl$_2$[d] | 0.119 | 0.7 (1) | 0.6 (1) | 1.1 (1) | n | n |
| [Ag$_2$(d2pype)$_4$](NO$_3$)$_2$[d] | 0.178 | n | n | n | n | n |
| [Cu$_2$(d2pype)$_4$]Cl$_2$[d] | 0.641 | n | n | n | n | n |
| [Au(2-pyppe)$_2$]Cl | 13.753 | 0.1 (1) | 0.1 (1) | 0.2 (1) | n | n |
| [Au(dppe)$_2$]Cl | 25.41 | n | n | n | n | n |
| Rhodamine | 0.34[e] | 3 (1) | 1 (1) | 1 (1) | 0.9 (1) | 0.5 (1) |
| Cisplatin | | 0.26 ± 0.1[f] | 1.2 ± 0.4[f] | 2.1 ± 0.1[g] | 0.11 ± 0.01[f] | 0.71 ± 0.2[f] |

TABLE 3

Human ovarian tumour cell line panel

| Cell line pair | CH1/CH1 cisR | 41M/41M cisR | 41M/SKOV3 |
|---|---|---|---|
| resistance type | acquired | acquired | intrinsic |
| resistance mechanism | increased DNA repair | reduced transport | increased cellular glutathione |

LEGENDS
TABLE 1
¶ Metal co-ordination compounds of ligands of Formula II, where; R$_1$–R$_4$=4-pyridyl (d4pype); R$_1$–R$_4$=3-pyridyl (d3pype); R$_1$–R$_4$=2-pyridyl (d2pype); R$_1$=R$_3$=Ph, R$_2$=R$_4$=2-pyridyl (2-pyppe); R$_1$–R$_4$=Ph (dppe)
  [a] average of two determinations at concentrations between 20 and 60 $\mu M$ in water plus octanol
  [b] mean ± SD or individual values when n<3; (n)
  [c] compound of formula V exists in solution as bis-chelated tetrahedral complex [Au(d3pype)$_2$]Cl (formula I)
  [d] compound exists as a dimer [M(P-P)]$_2$$^{2+}$ (formula III) in the solid state, but in solution exists as an equilibrium mixture of compounds of formula I, formula III, and formula IV
  [e] partition co-efficient from Chen in *Cancer Cells* 1: *The Transformed Phenotype*, pp 75–86 Cold Spring Harbour Press, N.Y.
  [f] ID$_{37}$ data from Ying Dong et al. submitted for publication
  [h] not determined.
TABLE 2
¶ Metal co-ordination compounds of ligands of formula II, where: R$_1$–R$_4$=4-pyridyl (d4pype); R$_1$–R$_4$=3-pyridyl (d3pype); R$_1$–R$_4$=2-pyridyl (d2pype); R$_1$=R$_3$=Ph, R$_2$–R$_4$=2-pyridyl (2-pyppe); R$_1$–R$_4$=Ph (dppe)
  [a] average of two determinations at concentrations between 20 and 60 $\mu M$ in water plus octanol
  [b] mean ± SD or individual values when n<3; (n)
  [c] compound of formula V exists in solution as bis-chelated tetrahedral complex [Au(d3pype)$_2$]Cl (formula I)
  [d] compound exists as a dimer [M(P-P)]$_2$$^{2+}$ (formula III) in the solid state, but in solution exists as an equilibrium mixture of compounds of formula I, formula III, and formula IV.

_e_ partition co-efficient from Chen in *Cancer Cells* 1: *The Transformed Phenotype*, pp 75–86 cold Spring Harbour Press: New York _f_ cytotoxicity data from Kelland et al., 1992, Cancer Research 52 3857–3864

_g_ cytotoxicity data from McKeage et al., 1994, Br. J. Cancer 69 1–7

_h_ not determined

BRIEF DESCRIPTION OF THE DRAWINGS

FIG. 1

Cytotoxicity of [Au(R$_2$P(CH$_2$)$_2$PR$_2$)$_2$]$^+$ Cl$^-$ (where R=4-pyridyl) against four human tumour cell lines in vitro.

ov=CI-80-13S ovarian
96L=MM96 melanoma
HeLa=HeLa cervical carcinoma
1A=HeLa-S1a

FIG. 2

Cytotoxicity of [Au$_2$(R$_2$P(CH$_2$)$_2$PR$_2$)$_2$Cl$_2$] (where R=3-pyridyl) against four human tumour cell lines in vitro ov=CI-80-13S ovarian
96L=MM96 melanoma
HeLa=HeLa cervical carcinoma
1A=HeLa-S1a

FIG. 3

Cytotoxicity of [Au$_2$(R$_2$P(CH$_2$)$_2$PR$_2$)$_4$)]Cl$_2$ (where R=2-pyridyl) against four human tumour cell lines in vitro ov=CI-80-13S ovarian
96L=MM96 melanoma
HeLa=HeLa cervical carcinoma
1A=HeLa-S1a

FIG. 4

Cytotoxicity of [Ag$_2$(R$_2$P(CH$_2$)$_2$PR$_2$)$_4$](NO$_3$)$_2$ (where R=2-pyridyl) against four human tumour cell lines in vitro ov=CI-80-13S ovarian
96L=MM96 melanoma
HeLa=HeLa cervical carcinoma
1A=HeLa-S1a

FIG. 5

Cytotoxicity of metal phosphine compounds against cisplatin-sensitive and -resistant ovarian tumours demonstrating the relationship between partition co-efficient and degree of selectivity and cytotoxic potency.

What is claimed is:

1. Compounds of the formula I:

wherein one to four of R$^1$, R$^2$, R$^3$, R$^4$, R$^5$, R$^6$, R$^7$ and R$^8$ are 4-pyridyl, 3-pyridyl, or 2-pyridyl, and the remaining R$^1$, R$^2$, R$^3$, R$^4$, R$^5$, R$^6$, R$^7$ and R$^8$ are phenyl and wherein:

A is selected from —(CH$_2$)—$_n$ where n is 2 or 3 or cis

M is Au(I), Ag(I) or Cu(I); and

X is a monovalent anion wherein said compound of formula I has selective toxicity to cancer cells and an octanol/water partition co-efficient between 0.01 and 25.5.

2. Compounds as claimed in claim 1 wherein all of R$_1$ through R$_8$ is 3-pyridyl.

3. Compounds as claimed in claim 1 wherein R$_1$, R$_2$, R$_5$ and R$_6$ is phenyl or substituted phenyl and R$_3$, R$_4$, R$_7$ and R$_8$ is 2-pyridyl.

4. Compounds as claimed in claim 1 wherein M is Aq(I) or Cu(I).

5. A method of treatment or inhibition of ovarian tumors, cervical tumors, lung cancer and melanoma including the step of administering the compound of claim 1 to a subject requiring such treatment wherein said compound has selective toxicity to cancer cells, wherein said compound is administered in an amount effective to treat or inhibit said tumors.

6. A pharmaceutical composition for treating or inhibiting tumors comprising a compound as defined in claim 1 in an amount effective to treat or inhibit tumors, as well as an inert pharmaceutically acceptable carrier or diluent.

7. A method as claimed in claim 5, wherein the compound is orally administered in the dose range of 10 mg to 150 mg/m$^2$ of body surface per day for one to five days.

8. A method as claimed in claim 5, wherein the compound is parenterally administered in the dose range of 5 mg to 50 mg/m$^2$ of body surface per day for one to five days.

9. The compounds of claim 1 wherein said monovalent anion is selected from the group consisting of nitrate, bromide, chloride and iodide.

* * * * *